United States Patent [19]

Shiragami et al.

[11] Patent Number: 5,310,895
[45] Date of Patent: May 10, 1994

[54] METHOD FOR PRODUCTION OF NUCLEOSIDE DERIVATIVES BY SELECTIVE HYDROLYSIS

[75] Inventors: Hiroshi Shiragami; Yasuhiro Tanaka; Hisao Iwagami, all of Kawasaki, Japan

[73] Assignee: Ajinomoto Co., Inc., Tokyo, Japan

[21] Appl. No.: 631,953

[22] Filed: Dec. 21, 1990

[30] Foreign Application Priority Data

Dec. 21, 1989 [JP] Japan .................................. 1-331951
Dec. 21, 1989 [JP] Japan .................................. 1-331952

[51] Int. Cl.⁵ .............................................. C07H 19/00
[52] U.S. Cl. .................................. 536/27.14; 536/27.6; 536/27.62; 536/27.63; 536/27.81; 536/28.2; 536/28.5; 536/28.53; 536/28.54; 536/103

[58] Field of Search ................. 536/23, 24, 103, 27.6, 536/27.62, 27.63, 27.81, 28.5, 28.53, 28.54

[56] References Cited

U.S. PATENT DOCUMENTS 3,817,982  6/1974  Verheyden et al. ............. 536/27.14

OTHER PUBLICATIONS

Kamiyama, Makoto, J.A.C.S., vol. III, pp. 3046–3050, (1989).

Primary Examiner—Johnnie R. Brown
Assistant Examiner—James O. Wilson
Attorney, Agent, or Firm—Oblon, Spivak, McClelland, Maier & Neustadt

[57] ABSTRACT

A method for selective hydrolysis of nucleoside derivatives using cyclodextrin in basic solution is disclosed.

32 Claims, No Drawings

METHOD FOR PRODUCTION OF NUCLEOSIDE DERIVATIVES BY SELECTIVE HYDROLYSIS

BACKGROUND OF THE INVENTION

Field of the Invention

The present invention relates to a method for production of nucleoside derivatives by selective hydrolysis.

Deoxynucleosides (III) through (VI), 2'-fluoro-2',3'-dideoxynucleosides (VII), 3'-fluoro-2',3'-dideoxynucleosides (VIII) and 2',3'-dideoxynucleoside derivatives shown by structural formula (IX) are obtained through selective hydrolysis:

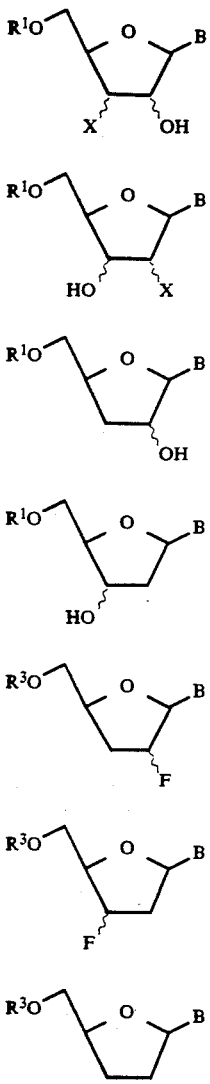

wherein B represents a nucleoside base; $R^1$ and $R^2$ are hydrolyzable acyl groups having 1 to 12 carbon atoms and $R^3$ represents a hydrolyzable acyl group having 1 to 12 carbon atoms or hydrogen; and X is a hydrogen atom, halogen atom, alkyl group having 1 to 12 carbon atoms or an acyloxy group having 1 to 12 carbon atoms.

The present nucleoside derivatives are known compounds which have antiviral activity or are useful as synthetic intermediates thereof (cf., for example, H. Mitsuya and S. Broader, *Proc. Natl. Acad. Sci.* USA, 83, 1911, 1986). *Discussion of the Background*

Extensive investigations have been made on synthetic reactions having high selectivity using cyclodextrin, which catalyzes bond cleavage reactions such as ester hydrolysis, amide hydrolysis, decarbonation, etc. Cyclodextrin forms a molecular complex with a reaction substrate and its chemical reaction proceeds as an interaction within the molecular complex. Therefore, cyclodextrin has been widely used as an enzyme model. The interaction between nucleotide and cyclodextrin has also been studied (Hoffmann et al., Biochemistry, 1970, 9, 3542). Komiyama et al. made further studies on the molecular complex between nucleoside and cyclodextrin and found a regioselective cleavage of 2',3'-cyclic monophosphate at the 2'-position by the catalyzing action of α-cyclodextrin (J. Am. Chem. Soc., 111, 3046, 1989). Recently, Uemura et al. found regioselective acylation of thymidine derivatives by enzyme. As described above, selective hydrolysis of nucleoside derivatives has become a target of important studies in recent years, not only in the field of synthetic chemistry but also in the fields of biochemistry and genetic engineering.

Deoxynucleosides (V) and (VI), 2'-fluoro-2',3'-dideoxynucleosides (VII) and 3'-fluoro-2',3'-dideoxynucleosides (VIII) and the 240 ,3'-dideoxynucleoside derivatives shown by formula (IX), described above, can be utilized as drugs for the treatment of AIDS, etc., so that keen attention has been paid to the compounds as having an antiviral activity (cf., Japanese Patent Application Laid-Open No. 61-280500 and J. Med. Chem., 30, 440 (1987)).

As a method for production of these nucleoside derivatives, for example, with respect to 3'-deoxynucleosides (V), there is known the method of Reese et al. (Synthesis, 304, 1983) which comprises subjecting 2'-acetyl-3'-bromoadenosine to radical reduction. With respect to 2'-deoxynucleosides (VI), the method of Todd et al. (J.C.S., 3035, 1958) is known. Further with respect to 2'-fluoro-2',3'-dideoxynucleosides (VII) and 3'-fluoro-2',3'-dideoxynucleosides (VIII), where is known a method for producing α-compounds which comprises fluorinating the hydroxy group of the nucleosides with inversion and subjecting the remaining hydroxy group to radical reduction; and regarding β-compounds, there has been found a method which comprises glycosylation of fluorinated sugar and nucleoside base (these methods are described in Biochemical Pharmacology, 36, 2719, 1987), and a method for synthesis which comprises treating 5'-tritylcordycepin (3-deoxyadenosine) with DAST (J. Med. Chem., 30, 2131, 1987), etc.

As methods for synthesis of the 2',3'-dideoxynucleoside derivatives (IX), there are known methods involving radical reduction (J. Med. Chem., 30, 862, 1987) or photoreduction (J. Am. Chem. Soc., 108, 3115, 1986); a method by applying olefination of diol (Corey-Winter reaction, J. Org. Chem., 54, 2217, 1989; Eastwood reaction, J. Org. Chem., 53, 5179, 1988), a method which comprises synthesis of dideoxy sugar followed by glycosylation (from glutamic acid, Tetrahedron Lett., 29, 1239, 1988; from D-mannitol, Nucleosides, Nucleotides, 903, 1989). As another important route, there is known a method using nucleoside derivatives having an acyloxy group and a halogen atom at the 2'- and 3'-positions (or at the 3'- and 2'-positions) as intermediates. The compounds are synthesized by the method of Moffatt et al. (J. Am. Chem. Soc., 95, 4025, 1973; U.S. Pat. No. 3,658,787 or J. Org. Chem., 39, 30, 1983); the method of Robins et al (J. Am. Chem. Soc., 98, 8213, 1976); the method of Engels (Tetrahedron Lett., 21, 4339, 1980); the method of Reese et al. (Synthesis, 304, 1983); the method disclosed in Japanese Patent Application Laid-Open No. 1-224390 which is a prior copending application filed by the same applicant. For synthesis of 2′,3′-dideoxynucleoside derivatives from the nucleoside derivatives, there is known a method of direct reduction using a palladium catalyst or a method via olefins (Moffatt et al., J. Org. Chem., 39, 30, 1974; U.S. Pat. No. 3,817,982; Robins et al., Tetrahedron Lett., 367, 1984).

As described above, various methods for synthesis of the 2′,3′-deoxynucleoside derivatives (V) have been developed but involve the following problems:

(a) expensive reactants are used;
(b) many products are formed;
(c) many reaction steps are involved;
(d) upon scaling up, problems are involved in operations of the reaction or treatment.

Therefore, it has been desired to develop an excellent method for synthesis of them.

DETAILED DESCRIPTION OF THE PREFERRED EMBODIMENTS

Upon synthesis of the nucleoside derivatives (V) through (IX), the present inventors have paid their attention to nucleoside derivatives (I) and (II) shown by structural formulas described below:

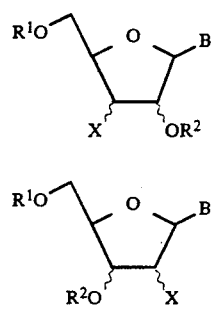

wherein B represents a nucleoside base; each of $R^1$ and $R^2$ represents a hydrolyzable acyl group having 1 to 12 carbon atoms; and X represents a hydrogen atom, a halogen atom, an alkyl group having 1 to 12 carbon atoms or an acyloxy group having 1 to 12 carbon atoms. The present inventors have made extensive investigations on selective hydrolysis of the acyl group in (I) and (II). As a result it has been found that by adding an appropriate inorganic salt to the nucleoside derivatives (I) and (II), in the presence of a cyclodextrin, hydrolysis selectively proceeds to give the nucleoside derivatives (III) and (IV) shown by the structural formulas described below:

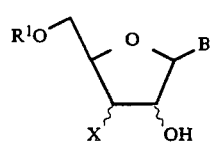

The 2′,3′-dideoxynucleoside derivatives are obtained by then converting the hydroxy group of the derivatives (III) or (IV) into a good leaving group and then further subjecting the compounds to hydrogenation or further hydrolysis thereby giving the desired 2′,3′-dideoxynucleoside derivatives (IX).

The present inventors have made further investigations on the utilization of the present invention and have also come to find a route for synthesis of the nucleoside derivatives (V) through (VIII) which are derived from the nucleosides (III) and (IV), obtained by selective hydrolysis as shown below.

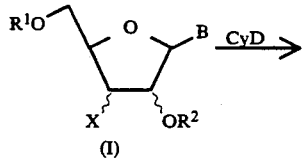

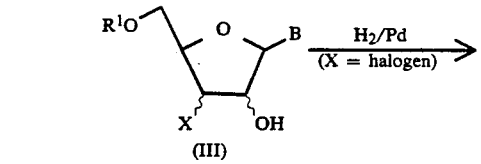

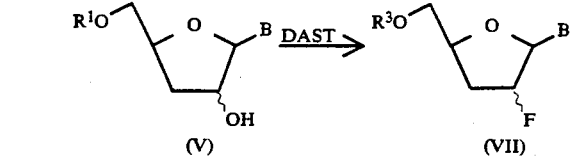

Compounds of formulas (IV), (VI) and (VIII) are obtained from the nucleosides (II) via a similar synthetic route.

In the formulas (I) through (VIII) described above, each of $R^1$, $R^2$, $R^3$ and $R^4$ independently represents an acyl group having 1 to 12 carbon atoms; X represents a halogen, and B represents a purine base bound to the sugar residue at the 9-position, a pyrimidine base bound to the sugar residue at the 1-position, an imidazole base bound to the sugar residue at the 1-position or a triazole base bound to the sugar residue at the 1-position.

Selective hydrolysis of the acyl group in nucleosides using cyclodextrin is unknown in nucleic acid chemistry. It is a novel and important discovery in the field of nucleic acid chemistry and in the field of synthetic chemistry.

In the present invention, the nucleoside base shown by B represents a purine base bound to the sugar residue at the 9-position, a pyrimidine base bound at the 1-position, an imidazole base bound at the i-position or a triazole base bound at the 1-position Examples of the acyl group shown by $R^1$ to $R^4$ include acetyl group, propionyl group, benzoyl group, etc., and examples of the halogen atom include fluorine, chlorine, bromine, and iodine. Examples of the purine base shown by B include adenine, guanine, hypoxanthine, xanthine, 6-chloropurine, 6-mercaptopurine, 6-methylthiopurine, 2,6-dichloropurine, 2-chloropurine, 2,6-diaminopurine, 2-amino-6-chloropurine, 2-aminopurine, etc.; examples of the pyrimidine base include uracil, cytosine, thymine, 5-fluorouracil, 5-chlorouracil, 5-bromouracil, 5-iodouracil, 5-ethyluracil, orothic acid, etc.; examples of the imidazole base include 5-amino-4-imidazole-3-carboxamide, etc; an example of the triazole base is 1,2,4-triazole-3-carboxamide. If necessary and desired, the amino groups in the base moiety may be protected.

Among the nucleoside derivatives (I) and (II) described above, 3'-deoxy-3'-bromo-2',5'-O-diacetyladenosine (X) may be synthesized, for example, by the method disclosed in Japanese Patent Application Laid-open No. 1-224390 which is a prior copending application filed by the same applicant. By adding an appropriate inorganic salt to Compound (X) in an aqueous solution of β-cyclodextrin, hydrolysis at the 2'-position proceeds highly selectively to give 5'-O-acetyl-3'-deoxy-3'-bromoadenosine (XI).

With respect to the cyclodextrin, each of the α-, β- and γ-compounds are useful alone or in combination; of these, β-cyclodextrin is particularly preferred. An aqueous solution in which the cyclodextrin is dissolved may also contain an organic solvent but the system of water alone is more preferable. As organic solvents, one or more of acetonitrile, ethylacetate and dioxan may be used. As the inorganic salt, hydrogencarbonates, carbonates, phosphates and the like may be used alone or in combination but among these inorganic salts, sodium hydrogencarbonate is particularly preferred. The amounts of water, cyclodextrin and the base used are in a range of 1 to 100 g/l, a range of 0.01 to 10 equivalents and a range of 0.1 to 10 equivalents, respectively, based on the starting material.

A ratio (K) of hydrolysis rate at the 2'-position to that at the 5'-position and a ratio of each compound produced are shown in Table 1, where the kind of the inorganic salt was varied.

TABLE 1

| run | Cyd | salt (1.25 eq) | K | (Epo) | (2',5'-OH) | (AcEpo) | (5'-OH) | (2'-OH) | (ABAR) |
|---|---|---|---|---|---|---|---|---|---|
| 1 | β(1.5) | NaHCO$_3$ | 85 | 0.4 | 1.4 | 2.4 | 0.8 | 85.1 | 9.2 |
| 2 | " | Na$_2$CO$_3$ | 24 | 3.8 | 9.8 | 25.8 | 0.2 | 57.9 | 1.0 |
| 3 | " | Na$_2$HPO$_4$ | 84 | 0.4 | 1.9 | 4.0 | 0.7 | 85.9 | 6.2 |
| 4 | " | AcONa | 24 | 0.2 | 0.1 | 0.1 | 0.4 | 15.3 | 83.6 |
| 5 | " | (NH$_4$)$_2$CO$_3$ | 30 | 2.1 | 9.5 | 20.1 | 0.2 | 65.9 | 1.0 |
| 6 | " | (NH$_4$)$_2$SO$_4$ | | | | | 0.7 | 4.1 | 94.2 |
| 7 | " | NH$_4$Cl | | | | | 0.8 | 2.5 | 95.6 |
| 8 | " | NaH$_2$PO$_4$ | | | | | 0.7 | 0.9 | 97.3 |
| 9 | " | SnCl$_2$ | | | | | 0.6 | 0.8 | 96.7 |
| 10 | α(1.5) | NaHCO$_3$ | 37 | | | | 0.5 | 17.2 | 79.2 |

Note 1) The reaction was carried out at room temperature for 3 hours.
Note 2) The K value indicates an assumed ratio of the hydrolysis rate at the 2'-Ac group to that at the 5'-Ac group.
Note 3) Numerical values for Epo (2',3'-epoxy compound), 2',5'-OH (3'-deoxy-3'-bromoadenosine), AcEPO (5'-acetyl-2',3'-epoxy compound), 5'-OH (2'-O-acetyl-3'-deoxy-3'-bromoadenosine), 2'-OH (5'-O-acetyl-3'-deoxy-3'-bromoadenosine) and ABAR (3'-deoxy-3'-bromo-2',5'-O-diacetyladenosine) are expressed in terms of HPLC Area.

As is clear from the table, the best selectivity of hydrolysis is obtained in the case of using sodium hydrogencarbonate or disodium hydrogenphosphate. If a salt is added to the same compound (X) in the absence of cyclodextrin the reaction does not proceed at all at room temperature. Even under heating conditions the hydrolysis is extremely slow and decomposition predominantly occurs. Furthermore, in the case of hydrolyzing with hydrochloric acid, hydrolysis predominantly occurs at the 5'-position and its rate ratio is approximately 6. In the case of hydrolysis with sodium hydroxide, the selectivity at the 2'-position is higher but its rate ratio is still only about 6. It is thus revealed that the hydrolysis at the 2'-position is selectively catalyzed by the presence of the cyclodextrin. $^1$H-NMR reveals that the adenine proton is shifted to a higher magnetic field by the addition of cyclodextrin. It is thus assumed that the adenine and the cyclodextrin form a molecular complex.

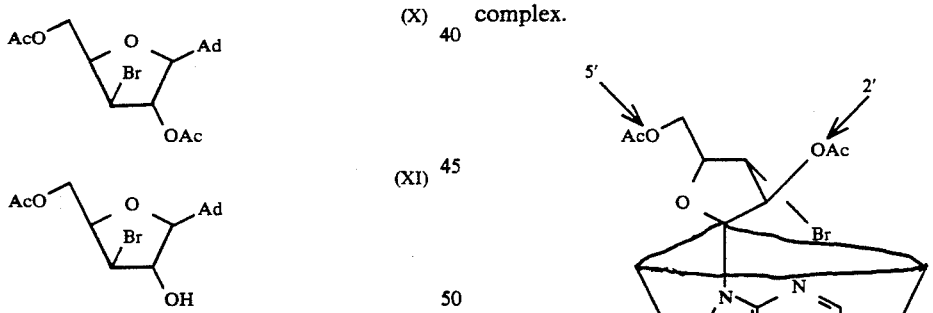

Further by protecting the 2'-position of (XI) with various substituents, a rate of the produced dideoxynucleosides to the deoxynucleosides in the palladium reduction can be markedly improved, as illustrated below.

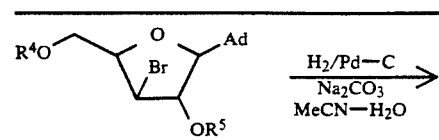

-continued

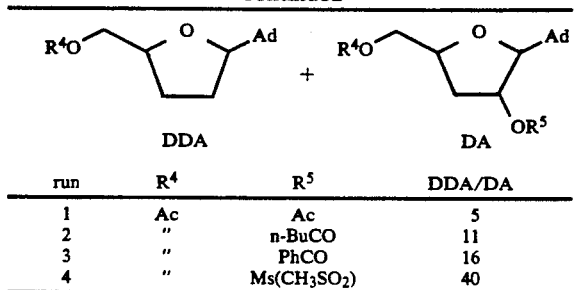

| run | R⁴ | R⁵ | DDA/DA |
|---|---|---|---|
| 1 | Ac | Ac | 5 |
| 2 | " | n-BuCO | 11 |
| 3 | " | PhCO | 16 |
| 4 | " | Ms(CH₃SO₂) | 40 |

The foregoing simple method for syntheses of the 2',3'-dideoxynucleoside derivatives (IX) (DDA), illustrates the utility of the selective hydrolysis using cyclodextrin and its high value. Next, Compound (XI) is subjected to hydrogenation in a solvent mixture of an organic solvent-water such as acetonitrile (MeCN) and sodium carbonate aqueous solution, in the presence of a palladium catalyst, whereby 3'-deoxy-5'-acetyl-5'-O-acetyladenosine (XI) can be selectively synthesized.

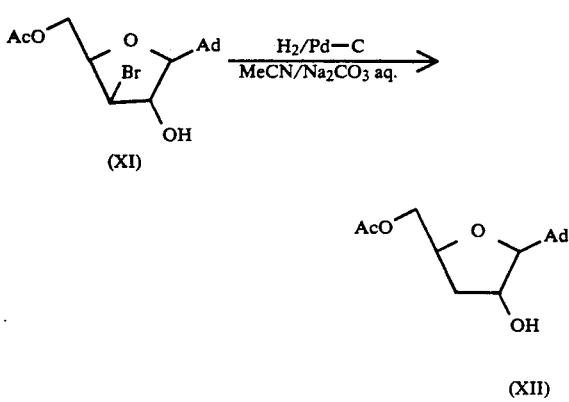

Where the reaction is carried out in the system using methanol as a solvent or triethylamine (Et₃N) as the base, the epoxy compound (Epo) is predominantly formed but the yield of Compound (XII) is greatly reduced (Table 2).

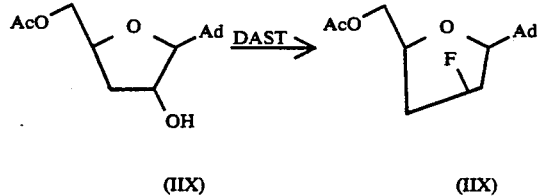

By finding the foregoing simple method for synthesis of the deoxynucleoside derivatives (V) and (VI), 2'-fluoro-2'-3'-dideoxynucleoside derivatives (VII) and 3'-fluoro-2',3'-dideoxynucleoside derivatives (VIII), it has been revealed that the utility of the selective hydrolysis using the cyclodextrin in accordance with the present invention is of high value. Hereafter the present invention is specifically described with reference to the examples, which are given for illustration of the invention and are not intended to be limiting thereof.

EXAMPLES

Example 1

After 50 g of β-cyclodextrin was added to 1 liter of water, the mixture was heated to completely dissolve. The solution was cooled to room temperature and 10 g of 3'-deoxy-3'-bromo-2',5'-O-diacetyladenosine was then added to the solution, and 2.5 g of sodium hydrogencarbonate was added to the mixture over 1 hour. After stirring was continued for further 2 hours, the reaction mixture was extracted 3 times with 500 ml of ethyl acetate. The solvent was distilled off to give 7 g (yield, 78%) of 5'-O-acetyl-3'-deoxy-3'-bromoadenosine ¹H-NMR data (300 MHz)

2.06 (3H, s), 4.37 (1H, brs), 4.39 (1H, brs), 4.57–4.64 (2H, m), 5.01 (1H, m), 5.89 (1H, d, J=4.03Hz), 6.51 (1H, d, J=5.13Hz), 7.33 (2H, brs), 8.17 (1H, s), 8.30 (1H, s) M.S. data MH+=373.

Example 2

After 1 g (2.7 mmols) of 5'-O-acetyl-3'-deoxy-3'-bromoadenosine was added to 10 ml of pyridine, 340 mg (1.1 eq.) of methanesulfonyl chloride was added to the mixture. The mixture was stirred at room temperature

TABLE 2

| Run | Compound (XII) | (Epo) | Time (Hr) | Catalyst (equivalent) | Catalyst (equivalent) | Solvent | Temperature |
|---|---|---|---|---|---|---|---|
| 1 | 82.0 | — | 8 | 10% Pd—C (0.05) | Na₂CO₃ (1.2) | MeCN—H₂O | 25° C. |
| 2 | 46.7 | 24.3 | 4 | 10% Pd—C (0.05) | Et₃N (1.2) | MeOH | 25° C. |
| 3 | — | 45.5 | — | 10% Pd—C (0.05) | Na₂CO₃ (1.2) | MeOH—H₂O | 25° C. | for 30 minutes and pyridine was distilled off under reduced pressure. The residue was added to 30 ml of water followed by extraction twice with 30 ml of chloroform. After the organic solvent was washed with water and then dried over magnesium sulfate, the solvent was distilled off under reduced pressure. The residue was purified by silica gel chromatography to give 1.09 g (yield, 90%) of 2'-O-mesyl-5'-O-acetyl-3'-deoxy-3'-bromoadenosine.

Furthermore, by reaction Compound (XII) with diethylaminosulfur trifluoride (DAST) in methylene chloride, 2'-(β)-fluoro-2',3'-dideoxyadenosine (XIII) can be synthesized.

¹H-NMR data 2.07 (3H, s), 3.38 (3H, s), 4.37–4.41 (2H, m), 4.61–4.66 (1H, m), 5.05–5.10 (1H, m), 5.99 (1H, d, J=5.5Hz), 6.18 (1H, d, J=4.5Hz), 7.43 (2H, brs), 8.19 (1H, s), 8.37 (1H, s) M.S. data MH+=451.

Example 3

After 1 g (2.7 mmols) of 5'-O-acetyl-3'-deoxy-3'-bromoadenosine was added to 10 ml of pyridine, 418 mg (1.1 eq.) of benzoyl chloride was added to the mixture. The mixture was stirred at room temperature for 2 hours and pyridine was distilled off under reduced pressure. The residue was added to 30 ml of water followed by extraction twice with 30 ml of chloroform. After the organic solvent was washed with water and then dried over magnesium sulfate, the solvent was distilled off under reduced pressure. The residue was purified by silica gel chromatography to give 1.18 g (yield, 92%) of 2'-O-benzoyl-5'-O-acetyl-3'-deoxy-3'-bromoadenosine.

$^1$H-NMR data 2.12 (3H, s), 4.50 (2H, m), 4.62 (2H, m), 6.01 (1H, s), 6.45 (1H, s), 7.51 (3H, m), 8.07 (2H, m), 8.31 (1H, s), 8.40 (1H, s) M.S. data MH+ =477.

Example 4

After 500 mg (1.1 mmol) of 2'-O-mesyl-5'-O-acetyl-3'-deoxy-3'-bromoadenosine was dissolved in 10 ml of acetonitrile, aqueous solution of sodium carbonate (141 mg (1.3 mmol) of Na$_2$CO$_3$ was dissolved in 2 ml of water) and 10% Pd/C (59 mg (5 mol %) on dry basis) were added to the solution. The mixture was stirred at room temperature for 2 hours under hydrogen atmosphere. It was confirmed by HPLC that the reaction was completed. Thereafter, the reaction solution was filtered and the residue was washed with 10 ml of water. The filtrate was combined with the washing liquid and the organic solvent was distilled off under reduced pressure. By adding 25% NAOH, pH was adjusted to 13. The system was stirred at room temperature for 30 minutes. The resulting solution was purified using synthetic adsorption resin SP-207 to give 183.5 mg (yield, 71%) of DDA. A:ratio of DDA to 3DA and 2DA formed in the reaction mixture was 62 (DDA/3DA+2DA=62).

$^1$H-NMR data 1.99–2.09 (1H, m), 2.19–2.27 (1H, m), 2.47–2.64 (2H, m), 3.65 (1H, dd, J=12.45, 5.13Hz), 3.82 (1H, dd, J=12.45, 3.10Hz), 4.35 (1H, m), 6.30 (1H, m), 8.18 (1H, s), 8.31 (1H, s) M.S. data MH+ =236.

Example 5

After 1.0 g (2.1 mmols) of 2'-O-benzoyl-5'-O-acetyl-3'-deoxy-3'-bromoadenosine was dissolved in 20 ml of acetonitrile, aqueous solution of sodium carbonate (267 mg (2.5 mmols) of Na$_2$CO$_3$ was dissolved in 4 ml of water) and 10% Pd/C (111 mg (5 mol %) on dry basis) were added to the solution. The mixture was stirred at room temperature for 2 hours under hydrogen atmosphere. It was confirmed by HPLC that the reaction was completed. Thereafter, the reaction solution was filtered and the residue was washed with 20 ml of water. The filtrate was combined with the washing liquid and the organic solvent was distilled off under reduced pressure. By adding 25% NAOH, pH was adjusted to 13. The system was stirred at room temperature for 30 minutes. The resulting solution was purified using synthetic adsorption resin SP-207 to give 345 mg (yield, 70%) of DDA. A ratio of DDA to 3DA and 2DA formed in the saponified solution was 16 (DDA/3DA+2DA=16).

Example 6

After 5 g of 5'-O-acetyl-3'-deoxy-3'-bromoadenosine (X) was dissolved in 100 ml of acetonitrile, 1.71 g of sodium carbonate (dissolved in 10 ml of water) and 1.5 g of Pd/C were added to the solution. The mixture was stirred at room temperature for 2 hours under hydrogen atmosphere of 3.5 atms. The reaction solution was filtered and the residue was washed with ethyl acetate. The filtrate was combined with the washing liquid. After the organic solvent was distilled off under reduced pressure, the formed crystals were taken out by filtration. The crystals were dissolved in 200 ml of ethyl acetate. The solution was dried over magnesium sulfate and the drying agent was removed. The system was concentrated to give 2.7 g (yield, 69%) of 3'-deoxy-5'-O-acetyladenosine (XII).

$^1$H-NMR data (300 MHz) 2.00 (3H, s), 2.01 (1H, m), 2.32 (1H, m), 4.19 (1H, dd, J=11.96, 3.17Hz), 4.26 (1H, dd, J=11.96, 5.86Hz), 4.53 (1H, m), 4.70 (1H, brs), 5.75 (1H, d, J=3.91Hz), 5.92 (1H, d, J=1.71Hz), 7.29 (2H, brs), 8.16 (1H, s), 8.25 (1H, s) M.S. data MH+ =294.

Example 7

After 300 mg (1.0 mmol) of 3'-deoxy-5'-O-acetyladenosine (XI) was suspended in 10 ml of methylene chloride, 0.5 ml (4.0 mmols) of DAST (diethylaminosulfur trifluoride) was added to the suspension. The mixture was mildly heated to reflux for 5 hours. After 30 ml of 10% sodium hydrogencarbonate aqueous solution was added to the mixture, extraction was carried out twice with 50 ml of methylene chloride. After the organic phase was dried over magnesium sulfate, the solvent was distilled off. The residue was purified by silica gel column chromatography (developing solvent: chloroform/methanol=24:1) to give 15 mg (yield, 5%) of 2'-β-fluoro-2'-3'-dideoxyadenosine (XIII).

$^1$H-NMR data (300 MHz) 2.05 (3H, s), 2.19–2.37 (1H, m), 2.61–2.81 (1H, m), 4.18–4.34 (2H, m), 4.39 (1H, m), 5.39 (1H, d, J$_{2,F}$=52.7Hz), 6.31 (1H, dd, J$_{1,F}$=17.8Hz), 7.26 (2H, brs), 8.08 (1H, d, J=2.4HZ), 8.10 (1H, s) M.S. data MH+ =296.

As is clear from the foregoing description the yield and purity of nucleoside derivatives can be improved and industrialization has become extremely advantageous. Thus, the present invention provides easy production of various substances such as dideoxynucleosides having pharmacological activities and greatly contributes to the medical industry.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for production of a nucleoside represented by the structure of formula (III) or (IV) which comprises selectively hydrolyzing a nucleoside compound represented by the structure of formula (I) or (II) in the presence of a cyclodextrin and an inorganic base to selectively convert said compound into a nucleoside compound (III) or (IV);

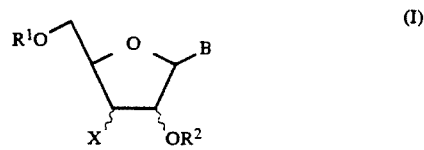

(I)

-continued

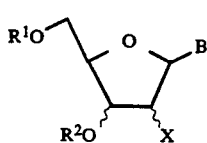 (II)

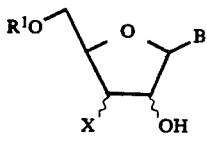 (III)

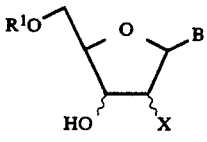 (IV)

wherein:
B: a nucleoside base
$R^1$, $R^2$: a hydrolyzable acyl group having 1 to 12 carbon atoms;
$R^3$: a hydrolyzable acyl group having 1 to 12 carbon atoms or hydrogen; and,
X: a hydrogen atom, a halogen atom, an alkyl group having 1 to 12 carbon atoms or an acyloxy group having 1 to 12 carbon atoms.

2. The process of claim 1, wherein said cyclodextrin is at least one member selected from the group consisting of α-cyclodextrin, β-cyclodextrin and γ-cyclodextrin.

3. The process of claim 1, wherein said inorganic base is at least one member selected from the group consisting of carbonate, hydrogencarbonate, acetate and phosphate.

4. The process of claim 1, wherein β-cyclodextrin is used as said cyclodextrin.

5. The process of claim 1, wherein sodium hydrogencarbonate is used as said inorganic base.

6. The process of claim 1, wherein said nucleoside base is any one of a purine base bound, to the sugar moiety, at the 9-position, a pyrimidine base bound at the 1-position, an imidazole base bound at the 1-position and a triazole base bound at the 1-position.

7. The process of claim 6, wherein said purine base is selected from the group consisting of adenine, hypoxanthine, guanine and xanthine.

8. The process of claim 6, wherein said pyrimidine base is selected from the group consisting of uracil, cytosine and thymine.

9. The process of claim 1, wherein both $R^1$ and $R^2$ represent an acetyl group.

10. The process wherein X is a member selected from the group consisting of fluorine, chlorine, bromine and iodine.

11. The process of claim 1, wherein sodium hydrogencarbonate is slowly added in the presence of the starting material and β-cyclodextrin thereby to increase the selectivity of hydrolysis at the 2°-position.

12. A process for the production of a dideoxynucleoside compound represented by the structure of formula (IX)

 (IX)

comprising:
(i) selectively hydrolyzing a nucleoside compound represented by the structure of formula (I) or (II) in the presence of a cyclodextrin and an inorganic base to selectively convert said compound into a nucleoside compound represented by the structure of formula (III) or (IV);

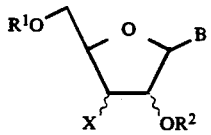 (I)

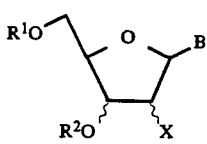 (II)

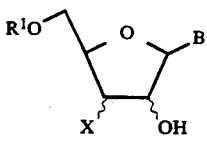 (III)

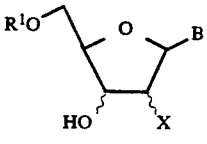 (IV)

wherein:
B: a nucleoside base
$R^1$, $R^2$: a hydrolyzable acyl group having 1 to 12 carbon atoms;
$R^3$: a hydrolyzable acyl group having 1 to 12 carbon atoms or hydrogen; and,
X: a hydrogen atom, a halogen atom, an alkyl group having 1 to 12 carbon atoms or an acyloxy group having 1 to 12 carbon atoms;
(ii) converting the hydroxyl groups of said nucleoside compound (III) or (IV) into a group capable of being replaced by hydrogen and,
(iii) subjecting said nucleoside compound to hydrogenation.

13. The process of claim 12, wherein said group capable of being replaced by hydrogen is selected from the group consisting of an acyl group having 1 to 12 carbon atoms, a sulfonyl group and an arylsulfonyl group.

14. The process of claim 13, wherein said acyl group is an aromatic acyl group selected from the group consisting of benzoyl, p-methoxybenzoyl, p-fluorobenzoyl, p-chlorobenzoyl, p-bromobenzoyl, and p-nitrobenzoyl groups, or is an aliphatic acyl group selected from the group consisting of trichloroacetyl, trifluoroacetyl, propionyl, butyryl, valeryl, and pivaloyl groups.

15. The process of claim 13, wherein said sulfonyl group is selected from the group consisting of methanesulfonyl, trifluoromethanesulfonyl and p-toluenesulfonyl groups.

16. A process for the production of a nucleoside compound represented by the structure of formula (V) or (VI):

(V)

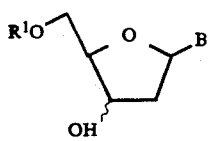

(VI)

wherein B is a nucleoside base and $R^1$ is a hydrolyzable acyl group having 1 to 12 carbon atoms comprising:

(i) selectively hydrolyzing a nucleoside compound represented by the structure of formula (I) or (II) in the presence of a cyclodextrin and an inorganic base to selectively convert said compound into a nucleoside compound represented by the structure of formula (III) or (IV);

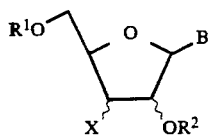

(I)

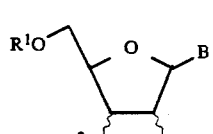

(II)

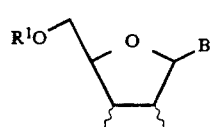

(III)

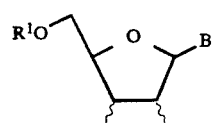

(IV)

wherein:
B: a nucleoside base
$R^1$, $R^2$: a hydrolyzable acyl group having 1 to 12 carbon atoms;
$R^3$: a hydrolyzable acyl group having 1 to 12 carbon atoms or hydrogen; and
X: a hydrogen atom or a halogen atom;

(ii) subjecting said nucleoside (III) wherein X is a halogen or (IV) wherein X is a halogen to hydrogenation.

17. The process of claim 16, wherein said nucleoside base is selected from the group consisting of a purine base bound to the sugar moiety, at the 9-position, a pyrimidine base bound at the 1-position, an imidazole base bound at the 1-position and a triazole base bound at the 1-position.

18. The process of claim 17, wherein said purine base is selected from the group consisting of adenine, hypoxanthine, guanine and xanthine.

19. The process of claim 17, wherein said pyrimidine base is selected from the group consisting of uracil, cytosine and thymine.

20. The process of claim 16, wherein $R^1$ represents an acetyl group.

21. The process of claim 16, wherein X is selected from the group consisting of fluorine, chlorine, bromine and iodine.

22. The process of claim 16, wherein said hydrogenation is carried out in an organic solvent-water mixture.

23. The process in claim 22, wherein at least one member of the group consisting of acetonitrile, ethyl acetate and dioxan is used as said organic solvent.

24. The process of claim 16, wherein a base is allowed to be present upon hydrogenation.

25. The process in claim 24, wherein at least one member of the group consisting of carbonate, hydrogencarbonate, acetate and phosphate is used as said base.

26. The process of claim 16, wherein palladium is used as a catalyst for said hydrogenation.

27. A process for the production of a nucleoside compound represented by the structure of formula (VII) or (VIII):

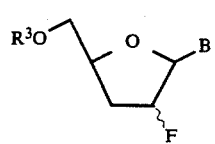

(VII)

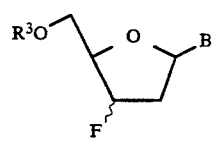

(VIII)

wherein B is a nucleoside base and $R^3$ represents a hydrolyzable acyl group having 1 to 12 carbon atoms or hydrogen comprising:

(i) selectively hydrolyzing a nucleoside compound represented by the structure of formula (I) or (II) in the presence of a cyclodextrin and an inorganic base to selectively convert said compound into a nucleoside compound represented by the structure of formula (III) or (IV);

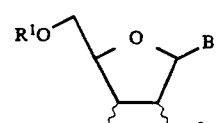

(I)

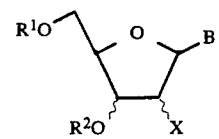

(II)

-continued

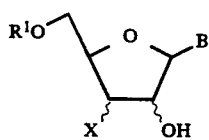
(III)

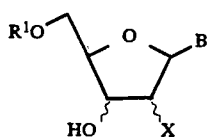
(IV)

wherein:

B: a nucleoside base $R^1$, $R^2$: a hydrolyzable acyl group having 1 to 12 carbon atoms;

$R^3$: a hydrolyzable acyl group having 1 to 12 carbon atoms or hydrogen; and

X: a hydrogen atom or a halogen atom;

(ii) subjecting said nucleoside compound (III) wherein X is a halogen or (IV) wherein X is a halogen to hydrogenation to produce a nucleoside compound represented by the structure of formula (V) or (VI)

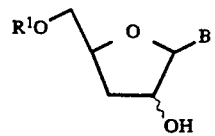
(V)

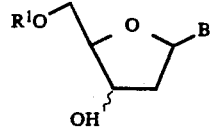
(VI)

(iii) and further reacting said nucleoside compound (V) or (VI) with a fluorinating agent.

28. The process of claim 27, wherein said nucleoside base is anyone of a purine base bound, to the sugar moiety, at the 9-position, a pyrimidine base bound at the 1-position, an imidazole base bound at the 1-position and a triazole base bound at the 1-position.

29. The process of claim 28, wherein said purine base is selected from the group consisting of adenine, hypoxanthine, guanine and xanthine.

30. The process of claim 28, wherein said pyrimidine base is selected from the group consisting of uracil, cytosine and thymine.

31. The process of claim 27, wherein both $R^1$ and $R^3$ represent an acetyl group.

32. The process of claim 27, wherein diethylaminosulfur trifluoride is used as said fluorinating agent.

* * * * *